United States Patent [19]

Miller et al.

[11] Patent Number: 4,650,918

[45] Date of Patent: Mar. 17, 1987

[54] ALKYLATION AIDE FOR SULFURIC ACID CATALYZED ALKYLATION UNITS

[76] Inventors: Richard F. Miller, Humble; Marilyn W. Blaschke, Pearland, both of Tex.

[21] Appl. No.: 801,271

[22] Filed: Nov. 25, 1985

[51] Int. Cl.$^4$ .............................................. C07C 2/58
[52] U.S. Cl. ..................................... 585/458; 585/730
[58] Field of Search ............................... 585/458, 730

[56] References Cited

U.S. PATENT DOCUMENTS 3,887,635  6/1975  Parker et al. ..................... 585/721
4,467,132  8/1984  Go et al. ........................... 585/724

Primary Examiner—Curtis R. Davis
Attorney, Agent, or Firm—Coleman R. Reap

[57] ABSTRACT

Hydrocarbon alkylation processes which are catalyzed by acids are promoted by the addition of an alkylation promoter which is a combination of a new carboxylic acid having the structural formula

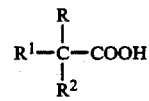

wherein R, $R^1$ and $R^2$ are alkyl groups and at least one aromatic hydrocarbon sulfonic acid selected from compounds having the structure

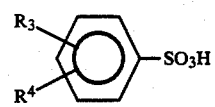

wherein $R^3$ is H or an alkyl group and $R^4$ is an alkyl group.

8 Claims, No Drawings

ALKYLATION AIDE FOR SULFURIC ACID CATALYZED ALKYLATION UNITS

FIELD OF THE INVENTION

This invention relates to a process for alkylating hydrocarbons and more particularly to an improved process of alkylating aliphatic hydrocarbons, particularly branched-chain aliphatic hydrocarbons with olefinic hydrocarbons in the presence of a strong acid.

BACKGROUND

The value of hydrocarbons can often be enhanced by alkylation of lower hydrocarbons to produce higher molecular weight hydrocarbons. For example, isobutanes can be alkylated with isobutene to produce isooctane, which is valuable for increasing the octane rating of gasoline. A common commercial method for alkylating a hydrocarbon is to react the hydrocarbon with selected olefins in the presence of a strong acid, such as sulfuric acid. Unfortunately, such acid, solutions are not readily miscible with organic liquids. Consequently, in alkylation processes catalyzed by strong acids, it has been necessary to use a considerable excess of acid to effect a commercially feasible degree of alkylation. The unused acid is discarded with the spent acid, thereby reducing the efficiency of the process and augmenting the already burdensome waste disposal problem. Improvements which will reduce the amount of acid waste have long been sought.

PRIOR ART

In attempts to improve the efficiency of acid catalyzed alkylations reaction temperatures have been lowered, the mixing efficiency has been increased and the ratio of hydrocarbon to olefin has been varied. None of these techniques has meet with significant success.

Chemical approaches have also been attempted. For example, various chemicals have been added to acid-catalyzed alkylation reaction mixtures to promote more efficient use of the acid catalyst. Thus, U.S. Pat. No. 3,324,196, issued to Kramer et al, discloses the use of an amine or amide containing at least one $C_8$ to $C_{20}$ aliphatic group to promote the acid-catalyzed alkylation of aliphatic and aromatic hydrocarbons. U.S. Pat. No. 2,880,255 discloses the use of mercaptans or combinations of aliphatic amines and mercaptans to promote the alkylation of hydrocarbons.

Carboxylic acids have also been used to promote acid-catalyzed alkylation reactions. For example, U.S. Pat. No. 3,778,489 discloses the use of carboxylic acids having 1 to 10 carbon atoms as promoters for the sulfuric acid-catalyzed alkylation of a paraffin with a combination of olefins. U.S. Pat. No. 3,766,293 discloses the use of carboxylic acids having 2 to 10 carbon atoms as promoters for the flurosulfuric acid-catalyzed alkylation of a paraffin with an olefin. U.S. Pat. No. 2,286,184 discloses the use of low molecular weight mono-carboxylic and dicarboxylic acids as modifiers for the sulfuric acid catalyzed alkylation of isoparaffins and olefins.

The present invention is based on the use of certain organic to promote alkylation reactions. It has been discovered that these organic acids increase the efficiency of acid-catalyzed alkylation reactions. Accordingly, it is an object of the invention to present an improved alkylation process. It is another object of the invention to present an improved process for alkylating hydrocarbons with acid catalyst. It is another object of the invention to reduce the acid consumption in acid-catalyzed alkylation reactions. These and other objects of the invention are supported in the following description and examples of the invention.

SUMMARY OF THE INVENTION

It has now been discovered that the highly efficient alkylation of aliphatic hydrocarbons by means of strong acid catalysts can be effected by carrying out the alkylation reaction in the presence of a mixture of at least one neo carboxylic acid having the structure

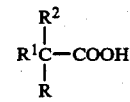

wherein R, $R^1$ and, $R^2$ are alkyl groups and the average total sum of the carbon atoms in R, $R^1$ and, $R^2$ usually varies from 3 to about 30 or more and at least one aromatic hydrocarbon sulfonic acid. In preferred neo carboxylic acids R, $R^1$ and $R^2$ contain an average total of 3 to about 10 carbon atoms. Preferred aromatic hydrocarbon sulfonic acids are the alkyl-substituted benzene sulfonic acids. Particularly preferred aromatic sulfonic acids contain 1 to about 16 total alkyl carbon atoms.

DETAILED DESCRIPTION

Suitable Neo acids useable in the invention are commercially available from Exxon Chemical Company under the name Neo Acids or from Shell Chemical Company under the name Versatic Acids ® or they may be prepared by methods such as described in the article "Neoacids" by Feffer, Journal of the American Oil Chemists Society, 55 342A (1978). The method of preparation of the neo acids is well known and forms no part of this invention.

The neo acid may be a pure acid or a mixture of isomers of a neo acid or it may be a mixture of various molecular weight neo acids. The average total number of carbon atoms in the alkyl radicals attached to the alpha carbon atom of these acids may range as high as 30 or more. The average of the total number of carbon atoms in the alpha alkyl radicals is desirably in the range of 3 to about 30 carbon atoms. When the neo acid is trimethyl acetic acid the sum of R, $R^1$ and $R^2$ will, of course, be 3. Preferred neo acids are those in which the average total number of carbon atoms in R, $R^1$ and $R^3$ is 3 to 10.

Typical neo acids that fall within the above description include neopentanoic acid, mixed neodecanoic acids, 2,2-dimethyl heptadecanoic acid, triethyl acetic acid, dimethyl pentyl acetic acid, etc. Preferred neo acids are trimethyl acetic acid and the pure or mixed neodecanoic acids.

Aromatic sulfonic acids usable in this invention include the aromatic hydrocarbon sulfonic acids having 7 to about 46 or more carbon atoms. Although sulfonic acids having more than 46 carbon atoms can be used in the invention sulfonic acids having no more than about 46 carbon atoms are preferred because they are more readily available and are easier to handle. In the preferred embodiment the aromatic hydrocarbon sulfonic acid has 1 to about 16 aliphatic carbon atoms. The most common aromatic sulfonic acids include the saturated and ethylenically unsaturated aliphatic hydrocarbon-substituted benzene sulfonic acids having 1 to about 40 aliphatic carbon atoms. As can be appreciated mixtures of two or more aromatic hydrocarbon sulfonic acids can be used in the invention. Suitable aliphatic hydrocarbon-substituted benzene sulfonic acids include those having the formula

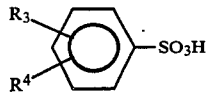

wherein $R^3$ is hydrogen or a straight or branched chain saturated or ethylenically unsaturated aliphatic hydrocarbon group and $R^4$ is a straight or branched chain saturated or ethylenically unsaturated aliphatic hydrocarbon group. The total number of carbon atoms in $R^3$ and $R^4$ generally varies from 1 to about 40 and preferably varies from 1 to about 16. When $R^3$ and $R^4$ are both aliphatic hydrocarbon groups they can be identical or different. The aliphatic hydrocarbon groups may be in any ring position relative to the sulfonic acid radical but in the preferred embodiment one group is in the para position. Typical aromatic sulfonic acids include p-toluene sulfonic acid, p-t-butyl benzene sulfonic acid, mixed dodecyl benzene sulfonic acids, o-hexadecylbenzene sulfonic acid, p-eicosyl benzene sulfonic acid, mixed xylene sulfonic acids, o-methyl-m-di-dodecyl benzene sulfonic acid, etc. The preferred aromatic hydrocarbon sulfonic acids are the alkyl-substituted benzene sulfonic acids, such as p-toluene sulfonic acid, p-t-butyl sulfonic acid, p-dodecyl benzene sulfonic acid, etc.

The preparation of the aromatic hydrocarbon sulfonic acids is well known and forms no part of this invention. Several aromatic hydrocarbon sulfonic acids are available commercially.

The carboxylic/sulfonic acid mixture may be used in any acid-catalyzed alkylation reaction between hydrocarbons and olefins. Hydrocarbons which are often alkylated include saturated aliphatic and cycloaliphatic hydrocarbons and aromatic hydrocarbons. The alkylation promoters of the invention are particularly useful in the alkylation of lower branched-chain alkanes, such as isobutane and isopentane, with lower olefins to produce octane rating improving additives for gasoline. Lower alkanes which are desirably alkylated include those having 4 to 10 atoms.

Olefins which are used in alkylation reactions include those monoolefins having 3 to 10 carbon atoms. The olefins may be straight- or branched-chain and the olefinic unsaturation may be located anywhere in the structure of the molecule.

Particularly useful gasoline additives for increasing the octane rating are the branched octanes, such as the compounds or mixture of compounds obtained when isobutane is alkylated with mixed butenes. Branched octanes can also be prepared by the reaction of other alkanes and olefins, for example by the reaction of isopentane and propylene.

Various strong acids are useful for catalyzing the alkylation of aliphatic or aromatic hydrocarbons with an olefin. Sulfuric acid, because of its efficiency and low cost, is the most commonly used acid alkylation catalyst. Other strong acids which can be used include hydrofluoric acid, phosphoric acid and fluorosulfonic acid. Any of the other well known strong acids are also useful for catalyzing alkylation reactions. Strong Lewis acids, such as aluminum bromide, aluminum chloride, antimony pentafluoride, antimony pentachloride, boron trifluoride, etc., can also be used as the acid catalyst in the process of this invention. In general, the alkylation promoters of the invention can be used with any known acid alkylation catalyst.

The alkylation reaction is carried out with all of the reactants in the liquid phase. The temperature of the reaction is that generally used for alkylation reactions. Reaction temperatures can vary from below 0° to as high as or higher than 200° F. The pressure of the reaction is not critical and any pressure which will maintain the reactants substantially in the liquid phase may be employed. Pressures generally range from atmospheric to as high as 100 psi or higher.

The neo acid and sulfonic acid components are generally used in relative concentrations of about 95 to 40% neo acid and 5 to 60% sulfonic acid, and preferably about 80 to 50% neo acid and 20 to 50% sulfonic acid, based on the total weight of neo acid and sulfonic acid used in the invention.

The total amount of alkylation promoter added to the reaction mixture usually varies from about 0.0005 to 5.0 weight percent, based on the total weight of catalyzing acid present in the reaction mixture. Amounts less than 0.0005 weight percent generally produce insignificant results and amounts greater than about 5.0 weight percent are generally unnecessary, although such higher concentrations can be used, if desired. The preferred promoter lower concentration is about 0.001 percent and the most preferred minimum level is about 0.0025 percent, based on the total weight of acid catalyst in the reaction mixture. The preferred upper limit of the alkylation promoter concentration is about 1.0 percent and the most preferred upper limit is about 0.5 percent, based on the total weight of acid catalyst in the reaction mixture. The optimum total amount of alkylation promoter will, of course, vary depending upon the particular promoters employed, the particular strong acid catalyst used and the particular hydrocarbons and olefins being reacted.

The alkylation promoters of the invention may be used with other additives, if desired. For example, other alkylation promoters may be used in combination with the promoters of the invention or surfactants or other agents may be added to the reaction mixture.

In a typical application of the invention the hydrocarbon to be alkylated, such as a lower branched-chain alkane, and an olefin are introduced into a suitable alkylation reaction vessel at a controlled temperature, usually in the range of about 40° to 60° F., and at a pressure sufficiently high to maintain the reactants in the liquid state. The ratio of alkylatable hydrocarbon to olefin alkylating agent is preferably maintained at a high ratio, e.g. about 10:1, to minimize the amount of alkyl sulfate formed by the reaction of olefin with sulfuric acid. An acid alkylation catalyst, such as sulfuric acid, and the alkylation promoters are introduced into the reactor, preferably on a continuous basis. At the end of the desired reaction period the finished product is removed from the reaction vessel and separated from the spent acid. The reaction may be carried out on either a batch or continuous basis.

The invention is further illustrated in the following examples. Unless indicated otherwise, parts and percentages are on a weight basis. The mixed neodecanoic acid used in the example is sold by Exxon Chemical Company and has an acid number of about 320 and a melting point of less than −40° C. This product has a structure of

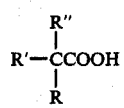

and a typical source distribution of
(i) R=CH$_3$, R'=CH$_3$, R''=C$_6$H$_{13}$: ... 31%
(ii) R<C$_6$H$_{13}$, R'=CH$_3$, R''>CH$_3$: ... 67%
(iii) R<C$_6$H$_{13}$, R'>CH$_3$, R''>CH$_3$: ... 2%

EXAMPLE

The efficiency of an alkylation reaction is dependent upon the contact time between the alkylation catalyst and the hydrocarbon being alkylated; the longer the contact time, the more efficient the alkylation reaction. The alkylation aide increases the catalyst-hydrocarbon contact time. This demonstrates the effectiveness of the alkylation aides of the invention. The test procedure is as follows: Fifty ml of 98% H$_2$SO$_4$ ml of iso-octane are introduced into a 100 ml graduate cylinder having a ground glass stopper. In the control run no alkylation additive is used and in the comparative runs and the run illustrating the invention 500 ppm of alkylation aide are added to the test mixture. The stoppered cylinder is mechanically shaken for 60 seconds after additive introduction and the time required for the entrained H$_2$SO$_4$ to separate from the hydrocarbon layer and the time required for the entrained hydrocarbon to separate from the H$_2$SO$_4$ layer are measured. The results are tabulated in the table.

TABLE

| Run | Additive | Conc. (ppm) | Separation Time (sec.) Hydrocarbon | H$_2$SO$_4$ |
|---|---|---|---|---|
| 1 | None (Control) | — | 2.38 | 3.24 |
| 2 | Mixed Neodecanoic acid (98%) (Comparative) | 500 | 13.86 | 44.50 |
| 3 | Para toluene sulfonic acid (Comparative) | 500 | 21.63 | 33.61 |
| 4 | Acid mixture (50% mixed neodecanoic acid, 50% para toluene sulfonic acid) | 500 | 26.69 | 52.74 |

As illustrated in the example, use of the alkylation aide of the invention (Run 4) results in a significantly greater contact time in both the hydrocarbon and H$_2$SO$_4$ phases than does the use of the same amount of the neodecanoic acid or the para toluene sulfonic acid alone (Runs 2 and 3).

Although the invention is described with particular reference to specific examples it is understood that the invention includes variations. For example, other hydrocarbons, such as aromatic compounds, may be alkylated or other olefins or acids may be used. The scope of the invention is limited only by the breadth of the appended claims.

What is claimed is:
1. In an alkylation process comprising contacting an alkylatable hydrocarbon with an olefinic alkylating agent at alkylation conditions in the presence of an acid catalyst and an alkylation promoter, the improvement comprising using in combination as the promoter
   (a) at least one carboxylic acid having the structure

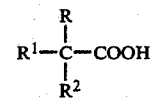

wherein R, R$^1$ and R$^2$ are the same or different straight or branched chains alkyl groups and the average total sum of carbon atoms in R, R$^1$ and R$^2$ is 3 to 30, and
   (b) at least one aromatic hydrocarbon sulfonic acid having 7 to 46 carbon atoms.
2. The improved process of claim 1 wherein the average total sum of carbon atoms in R, R$^1$ and R$^2$ is 3 to 10.
3. The improved process of either of claims 1 or 2 wherein said aromatic hydrocarbon sulfonic acid has 1 to 16 aliphatic carbon atoms.
4. The improved process of either of claims 1 or 2 wherein said aromatic hydrocarbon sulfonic acid is selected from compounds having the structure

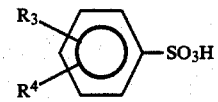

wherein R$^3$ is H or a straight- or branched-chain alkyl group and R$^4$ is a straight- or branched-chain alkyl group and the total number of carbon atoms in R$^3$ and R$^4$ is 1 'to 40.
5. In an alkylation process comprising contacting an alkylatable hydrocarbon with an olefinic alkylating agent at alkylation conditions in the presence of an acid catalyst and an alkylation promoter, the improvement comprising using in combination as the promoter
   (a) at least one carboxylic acid having the structure

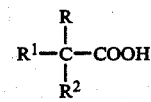

wherein R, R$_1$ and R$^2$ are the same or different straight- or branched-chain alkyl groups and the average total sum of carbon atoms in R, R$^1$ and R$^2$ is 3 to 30 and
   (b) at least aromatic hydrocarbon sulfonic acid selected from compounds having the structure

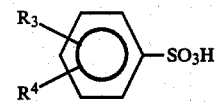

wherein R$^3$ is H or an alkyl group and R$_4$ is an alkyl group and the total number of carbon atoms in R$^3$ and R$^4$ is 1 to 40.
6. The improved process of claim 5 wherein the average total number of carbon atoms in R, R$^1$ and R$^2$ is 3 to 10.
7. The improved process of either of claims 5 or 6 wherein the total number of carbon atoms in R$^3$ and R$^4$ is 1 to 16.
8. The improved process of claim 7 wherein R$^3$ is H.

* * * * *